United States Patent
Lamberti et al.

(10) Patent No.: US 9,411,069 B1
(45) Date of Patent: Aug. 9, 2016

(54) WIRELESS RADIATION SENSOR

(71) Applicant: Consolidated Nuclear Security, LLC, Reston, VA (US)

(72) Inventors: Vincent E. Lamberti, Oak Ridge, TN (US); Layton N. Howell, Jr., Knoxvill, TN (US); David K. Mee, Knoxville, TN (US); Reid L. Kress, Oak Ridge, TN (US)

(73) Assignee: Consolidated Nuclear Security, LLC, Oak Ridge, TN (US)

( * ) Notice: Subject to any disclaimer, the term of this patent is extended or adjusted under 35 U.S.C. 154(b) by 0 days.

(21) Appl. No.: 14/842,007

(22) Filed: Sep. 1, 2015

Related U.S. Application Data (63) Continuation-in-part of application No. 14/493,811, filed on Sep. 23, 2014, which is a continuation-in-part of application No. 13/832,873, filed on Mar. 15, 2013, now Pat. No. 8,871,523.

(51) Int. Cl.
| | |
|---|---|
| *G01N 27/72* | (2006.01) |
| *G01N 27/74* | (2006.01) |
| *G01N 33/00* | (2006.01) |
| *G01V 5/00* | (2006.01) |
| *G01N 27/80* | (2006.01) |
| *G01N 33/20* | (2006.01) |

(52) U.S. Cl.
CPC ............. *G01V 5/0008* (2013.01); *G01N 27/80* (2013.01); *G01N 33/203* (2013.01); *G01N 27/72* (2013.01); *G01N 33/0057* (2013.01); *G01N 2033/0093* (2013.01); *Y10T 436/25875* (2015.01)

(58) Field of Classification Search
CPC .......... G01N 33/0004; G01N 33/0057; G01N 33/20; G01N 33/203; G01N 33/22; G01N 33/227; G01N 1/22; G01N 1/2273; G01N 27/72; G01N 27/74; G01N 27/80; G01N 2033/0093; Y10T 436/25875; G01V 5/0008
USPC ................. 436/73, 84, 149, 150, 151, 181; 422/68.1, 69, 83, 88
See application file for complete search history.

(56) References Cited

U.S. PATENT DOCUMENTS

| | | | |
|---|---|---|---|
| 5,821,129 A | 10/1998 | Grimes et al. | |
| 6,270,591 B2 | 8/2001 | Chiriac et al. | |
| 6,393,921 B1 | 5/2002 | Grimes et al. | |
| 7,694,346 B2 | 4/2010 | Adams | |
| 7,824,619 B1 | 11/2010 | Aviram | |
| 8,871,523 B1 * | 10/2014 | Lambert | G01N 33/00057 422/83 |
| 2006/0032289 A1 | 2/2006 | Pinnaduwage et al. | |
| 2006/0231420 A1 | 10/2006 | Garzon et al. | |

OTHER PUBLICATIONS

Skorvanek et al. Phys. Stat. Sol., vol. 99, 1987, pp. 275-278.*
Ong et al. Journal of IEEE Sensors, vol. 6, No. 3, Jun. 2006, pp. 514-523.*

(Continued)

*Primary Examiner* — Maureen Wallenhorst
(74) *Attorney, Agent, or Firm* — Luedeka Neely Group, P.C.

(57) ABSTRACT

Disclosed is a sensor for detecting radiation. The sensor includes a ferromagnetic metal and a radiation sensitive material coupled to the ferromagnetic metal. The radiation sensitive material is operable to change a tensile stress of the ferromagnetic metal upon exposure to radiation. The radiation is detected based on changes in the magnetic switching characteristics of the ferromagnetic metal caused by the changes in the tensile stress.

18 Claims, 5 Drawing Sheets

(56) References Cited

OTHER PUBLICATIONS

M.D. Allendorf, et al.; "Stress-Induced Chemical Detection Using Flexible Metal-Organic Frameworks"; J. Am. Chem. Soc. 130 (2008) 14404.
Chiriac, et al; "Effect of Glass Removal on the Magnetic Behavior of FeSiB Glass-Covered Wire"; IEEE Trans. Magn. 33 (1997) 782.
H. Chiriac, et al.; "Amorphous Glass-Covered Magnetic Wires: Preparation, Properties, Applications"; Progress in Materials Science, 1996, 40, 333-407.
C.A. Grimes, et al.; Wireless Magnetoelastic Resonance Sensors: A Critical Review, Sensors 2, (2002) 294.
C.A. Grimes, et al.; "Magnetoelastic Sensors in Combination with Nanometer-scale Honeycombed Thin Film Ceramic TiO2 for Remote Query Measurement of Humidity"; Journal of Applied Physics, 87 (2000).
C.A. Grimes,e t al.; "Remote Query Pressure Measurement Using Magnetoelastic Sensors"; Rev. Sci. Instrum. 70 (1999) 4711.
M. Han, et al.; "Sensors Development Using Its Unusual Properties of Fe/Co-Based |Amorphous Soft Magnetic Wire"; J. Mater. Sci. 40 (2005) 5573.
J. Kravcak, et al.; "The Analysis of Large Barkhausen Effect in the FeSiB Amorphous Wire"; Cxech. J. Phys. 52 (2002) 175.
H. Lai, et al.; Identification of Volatile Chemical Signatures from Plastic Explosives by SPME-GC/MS and Detection by Ion Mobility Spectometry, Anal. Bioanal. Chem. 396 (2010) 2997.
K. Mohri, et al.; "Advances of Amorphous Wire Magnetic over 27 Years"; Phys. Status Solidi A, 206, pp. 601-607, Feb. 2, 2009.
D.S. Moore; "Recent Advances in Trace Explosives Detection Instrumentation"; Sens. Imaging 8 (2007) 9.
D.S. Moore; "Instrumentation for Trace Detection of High Explosives"; Rev. Sci. Instrum. 75 (2004) 2499.
M. Nambayah, et al.; "A Quantitative Assessment of Chemical Techniques for Detecting Traces of Explosives at Counter-Terrorist Portals"; Talanta 63 (2004) 461.
K.G. Ong, et al.; "Quantification of Multiple Bioagents With Wireless, Remote-Query Magnetoelastic Microsensors"; IEEE SEnsors Journal, vol. 6, No. 3, Jun. 2006.
K.G. Ong, et al.; "A Wireless, Passive, Magnetically-soft Harmonic Sensor for Monitoring Sodium Hypochlorite Concentrations in Water"; Sensors 2003, pp. 11-18.
J.M. Perr, et al.; "Solid Phase Microextraction Ion Mobility Spectrometer Interface for Explosive and Taggant Detection"; J. Sep. Sci. 28 (2005) 177.
L.P. Shen, et al.; "Sensitive Stress-Impadence Micro Sensor Using Amorphous Magnetostrictive Wire"; IEEE Trans. Magn. 33 (1977) 3355.
J.I. Steinfeld, et al.; "Explosives Detection: A Challenge for Physical Chemistry", Annu. Rev. Phys. Chem. 49 (1998) 203.
M. Vazquez; "Soft Magnetic Wires"; Physica B 299 (2001)302.
M. Vazquez, et al.; "Magnetic Properties of Glass-Coated Amorphous and Nanocrystalline Microwires"; J. Magn. Magn. Mater. 160 (1996) 223.
A. Zhukov, et al.; "Microwires Coated by Glass: A New Family of Soft and Hard Magnetic Materials"; J. Mater. Res. 15 (2000) 2107.
J. Alderman, et al.; "Measurement of radiation-induced demagnetization of Nd—Fe—B permanent magnets"; Nuclear Instruments and Methods in Physics Research A 481 (2002), pp. 9-28.
S. Anderson, et al.; "Fast Neutron Damage Studies on NdFeB Materials"; Contirbuted to Particle Accelerator Conference (PAC05), Knoxville, TN, May 16, 2005.
S. Anderson, et al.; "Fast Neutron Radioactivity and Damage Studies on Materials"; http://www.slac.stanford.edu/grp/arb/tn/arbvol5/AARD472.pdf.
Z. Bell, et al.; "Neutron detection with cryogenics and semiconductors"; WILEY-VCH Verlag GmbH & Co. KGaA, Weinheim; phys. stat. sol. (c) 2, No. 5 (2005) / www.pss-c.com.
F. Bouquet, et al.; "Designer's guide to radiation effects on materials for use on Jupiter fly-bys and orbiters"; IEEE Transactions on Nuclear Science, vol. NS-26, No. 4, Aug. 1979.
F. Bouquet, et al.; "Radiation design considerations for advanced Jupiter spacecraft"; IEEE Transactions on Nuclear Science, Vo.. NS-26. No. 6, Dec. 1979.
F. Bouquet, et al.; "Radiation effects response data for synthetic organic insulation and dielectrics"; IEEE Transactions on Nuclear Science, vol. NS-31, No. 6, Dec. 1984.
F. Bouquet, et al.; "Radiation thresholds for synthetic elastomers"; IEEE Transactions on Nuclear Science, vol. NS-32, No. 6, Dec. 1985.
A. Caruso; "The physics of solid-state neutron detector materials and geometries"; Journal of Physics: Condensed Matter 22 (2010) 443201 (32pp).
J. Cost, et al.; "Effects of Neutron Irradiation on Nd—Fe—B Magnetic Properties"; IEEE Transactions on Magnetics, vol. 24, No. 3, May 1988.
US Gov't Accountability Office (GAO); "Technology Assessment—Neutron detectors: Alternatives to using helium-3"; Center for Science, Technology, and Engineering, Natural Resources and Environment, Report to Congressional Requesters; GAO-11-753, Sep. 2011.
P. Job, et al.; "Study of the radiation damage of Nd—Fe—B permanent magnets"; http://www.ipd.anl.gov/anlpubs/2002/02/42037.pdf.
R. Kouzes, et al.; "Status summary of 3He and neutron detection alternatives for homeland security"; Pacific Northwest National Laboratory, Prepared for the U.S. Department of Energy, PNNL-19360, Apr. 2010.
J. Laghari, et al.; "A Brief Survey of Radiation Effects on Polymer Dielectrics"; IEEE Transactions on Nuclear Science, vol. 37, No. 2, Apr. 1990.
J. Livingston; "Magnetomechanical Properties of Amorphous Metals"; Phys. Stat. Sol. 70 (1982) 591.
D. Park, et al.; "Effect of neutron irradiation on magnetic properties in the low alloy Ni—Mo steel SA508-3"; Journal of Applied Physics, 81, 4125 (1997).
E. Reichmanis, et al.; "Radiation Effects on Polymeric Materials"; ACS Symposium Series; American Chemical Society; Washington, DC, 1993.
A. Simpson, et al.; "A Review of Neutron Detection Technology Alternatives to Helium—3 for Safeguards Applications"; INMM 52nd Annual Meeting, Jul. 17-21, 2011, Palm Desert, California.
I. Skorvanek, et al.; "Influence of Neutron Irradiation on the Magnetic Properties of FeNiCrMoSiB Amorphous Alloys"; Phys. Stat. Sol. (A) 108 (1988) 747.
I. Skorvanek, et al.; "Effects of Neutron Irradiation on Magnetic Properties of Fe80B20 Amorphous Alloys"; Phys. Stat. Sol. (A) 108 (1988) 747.
M. Vazquez; "Advanced Magnetic Microwires"; Handbook of Magnetism and Advanced Magnetic Materials, vol. 4: Novel Materials, 2007.

\* cited by examiner

WIRELESS RADIATION SENSOR

CROSS-REFERENCE TO RELATED APPLICATION

This application is a continuation-in-part to U.S. application Ser. No. 14/493,811 filed Sep. 23, 2014, now U.S. Pat. No. 9,255,920, and entitled "Wireless Sensor," which claimed priority as a continuation-in-part to U.S. application Ser. No. 13/832,873 filed Mar. 15, 2013, now U.S. Pat. No. 8,871,523, and entitled "Wireless Sensor for Detecting Explosive Material," the entire contents of both being incorporated by reference herein.

GOVERNMENT RIGHTS

The U.S. Government has rights to this invention pursuant to contract number DE-NA0001942 between the U.S. Department of Energy and Consolidated Nuclear Security, LLC.

FIELD

This disclosure relates to the field of sensors for detecting radiation. More particularly, this disclosure relates to an inexpensive, highly sensitive radiation sensor having a sensing element capable of being embedded in unobtrusive objects and/or interrogated wirelessly.

BACKGROUND

Reliable detection and verification of nuclear materials through both overt and covert means are essential components of global nuclear security. Plutonium, highly enriched uranium, and other radioactive materials are typically identified by their characteristic neutron and gamma-ray radiation. The Department of Homeland Security (DHS) Domestic Nuclear Detection Office (DNDO) is continually searching for technologies that improve radiation detection capabilities and reduce costs.

For many field applications, radiation sensors must be sensitive toward weak signals, simple to operate and interpret, portable and rugged, and sufficiently inexpensive for many-unit purchases. Current technologies for neutron and gamma-ray radiation detection generally only satisfy some of these requirements. For example, gamma-ray detectors based on high-purity geranium (HPGe) exhibit excellent energy resolution, but their sensitivity is insufficient and they must be operated at cryogenic temperatures to achieve optimal performance. For thermal neutron detection, instruments employing helium-3 display high efficiency and good discrimination against concomitant gamma signals, but these sensors are large, require high voltage to operate, are sensitive to vibration, and rely on helium-3, which is experiencing a deepening worldwide shortage. Moreover, none of these technologies are very amenable to covert data collection.

SUMMARY

According to one embodiment of the disclosure, a radiation sensor includes a ferromagnetic metal and a radiation sensitive material coupled to the ferromagnetic metal. The radiation sensitive material is operable to change a tensile stress of the ferromagnetic metal upon exposure to radiation.

According to certain embodiments, the ferromagnetic metal is an amorphous wire. The amorphous wire in certain embodiments is composed of a cobalt and/or iron based alloy. In preferred embodiments, the amorphous wire is melt extracted.

According to certain embodiments, the sensor further includes a detection mechanism having an inducing mechanism to induce alternating magnetic domains in the ferromagnetic metal and a sensing mechanism to detect changes in magnetic switching characteristics of the ferromagnetic metal caused by the inducing mechanism and changes in the tensile stress of the ferromagnetic metal caused by exposure of the radiation sensitive material to radiation. According to preferred embodiments, the sensing mechanism detects changes in induced peaks along a time waveform resulting from the induced alternating magnetic domains in the ferromagnetic metal and changes in the tensile stress of the ferromagnetic metal; the detection mechanism is provided in a separate unit from the ferromagnetic metal and the radiation sensitive material; and/or no electrical components are physically connected to the radiation sensor.

According to some embodiments, the radiation sensitive material is directly coupled to the ferromagnetic metal. In other embodiments, the radiation sensitive material is operable to emit a gas upon exposure to radiation and the radiation sensitive material is indirectly coupled to the ferromagnetic metal via a molecular recognition reagent operable to change the tensile stress of the ferromagnetic metal upon exposure of the molecular recognition reagent to the emitted gas from the radiation sensitive material.

According to another embodiment of the disclosure, a radiation sensor includes a ferromagnetic metal having a tensile stress that is operable to change upon exposure to radiation and a detection mechanism. The detection mechanism includes an inducing mechanism to induce alternating magnetic domains in the ferromagnetic metal and a sensing mechanism to detect changes in magnetic switching characteristics of the ferromagnetic metal caused by the inducing mechanism and changes in the tensile stress of the ferromagnetic metal caused by exposure of the ferromagnetic metal to radiation.

According to certain embodiments, the ferromagnetic metal is an amorphous material composed of an iron-based alloy. In preferred embodiments, the sensing mechanism detects changes in induced peaks along a time waveform resulting from the induced alternating magnetic domains in the ferromagnetic metal and changes in the tensile stress of the ferromagnetic metal; the detection mechanism is provided in a separate unit from the ferromagnetic metal; and/or no electrical components are physically connected to the ferromagnetic metal.

According to yet another embodiment of the disclosure, a method of detecting radiation in a target device includes providing a sensor element including a ferromagnetic metal and a radiation sensitive material coupled to the ferromagnetic metal; placing the sensor element in proximity to or inside the target device such that the radiation sensitive material changes a tensile stress of the ferromagnetic metal upon exposure to radiation; and detecting a change in magnetic switching characteristics of the ferromagnetic metal resulting from the change in tensile stress imparted by the radiation sensitive material.

According to certain embodiments, the detecting step is performed by a detection mechanism configured to wirelessly interrogate the sensor element.

According to certain embodiments, the radiation sensitive material is operable to emit a gas upon exposure to radiation and the radiation sensitive material is indirectly coupled to the ferromagnetic metal via a molecular recognition reagent operable to change the tensile stress of the ferromagnetic metal upon exposure of the molecular recognition reagent to the emitted gas from the radiation sensitive material.

BRIEF DESCRIPTION OF THE DRAWINGS

Various advantages are apparent by reference to the detailed description in conjunction with the figures, wherein elements are not to scale so as to more clearly show the details, wherein like reference numbers indicate like elements throughout the several views, and wherein.

DETAILED DESCRIPTION

In the following detailed description of the preferred and other embodiments, reference is made to the accompanying drawings, which form a part hereof, and within which are shown by way of illustration the practice of specific embodiments of the disclosure. It is to be understood that other embodiments may be utilized, and that structural changes may be made and processes may vary in other embodiments. Further, it should be understood that this technology may be used in small, low-cost chemical sensors that have applications in many fields such as detecting materials used in making explosives, chemical and biological warfare agents, volatile organic compounds, poisons and toxins, diagnostic exhaled gases, temperature, waste stream contents, air and water pollutants and pathogens, food-borne pathogens, exhaled gases for diagnostics, pharmaceuticals and drugs (including narcotics), cadaverine, diaper contents, moisture, glucose (e.g., blood clot prediction), hazardous gases (e.g., carbon monoxide/natural gas for home detection, methane for coal mine safety, etc.), and countless other chemical substances for countless applications. A particular substance being detected is referred to herein as a "target material." The device or housing that potentially contains one or more target materials is referred to herein as a "target device."

Figure 1:
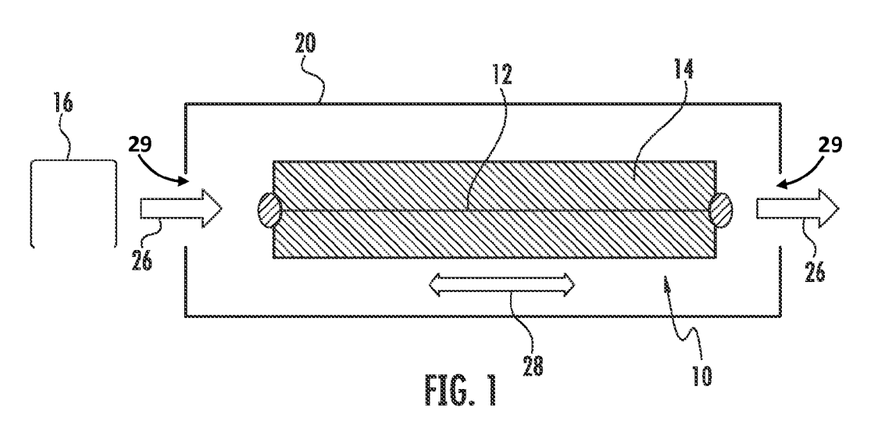
FIGS. 1 and 2 depict different embodiments of a sensing element having a ferromagnetic wire coupled with a molecular recognition reagent according to the disclosure.

Referring to FIG. 1, the sensor of the present disclosure includes a sensing element 10 that employs a ferromagnetic metal 12 coupled to a porous or perforated molecular recognition reagent 14. As shown in FIG. 1, the ferromagnetic metal in certain embodiments is configured as a mounted wire 12 and the molecular recognition reagent 14 is disposed around the wire. Alternatively, the molecular recognition reagent 14 could be coated onto the wire. A ribbon construction for the ferromagnetic metal may also be utilized within the spirit of the present disclosure. For purposes of illustration, the thickness of the molecular recognition reagent 14 in FIG. 1 has been greatly exaggerated with respect to the ferromagnetic wire 12. In typical embodiments, the wire 12 will be about 30 to about 100 microns in diameter and the molecular recognition reagent 14 will have a thickness greater than the wire 12. It should be understood that the term molecular recognition reagent 14 could refer to a specific material or a composite of more than one material.

In operation, the sensing element 10 is placed in proximity to a target device 16 such that the molecular recognition reagent 14 is exposed to vapor or liquid from the target material if the target material is present in the device 16. As shown in the embodiment of FIG. 1, the sensing element 10 may be disposed in a flow housing 20 having vent holes 29 such that the target material of the target device 16 flows through the housing 20 and past the sensing element 10 as indicated by arrows 26. The molecular recognition reagent 14 is characterized by its affinity for gaseous or liquid components of particular target materials, and its ability to exhibit a large volume change per unit of the target material absorbed. Thus, when detecting the target device 16, the molecular recognition reagent 14 expands upon exposure to the target material, which imposes stress on the ferromagnetic wire 12 in both directions indicated by arrow 28. In other embodiments, the molecular recognition reagent 14 contracts upon exposure to the target material such that the pre-stressed wire 12 loses tension upon exposure to the target material. Whether the tension of the wire 12 increases or decreases upon exposure to the target material, the sensing element 10 exploits the fact that, when subjected to alternating magnetic fields, the magnetic field strength and switching speed of the ferromagnetic wire 12 varies as a function of tensile stress in the ferromagnetic wire 12 caused by the volume change of the molecular recognition reagent 14.

In certain embodiments, the sensing element 10 will employ an array of ferromagnetic wires 12 coupled to a diverse set of molecular recognition reagents 14 such that each wire 12 will respond differently to each type or combination of target materials absorbed by the molecular recognition reagents 14. A neural network or other type of artificial intelligence based tool may then be employed to analyze and interpret the changes in the magnetic properties of the wires 12 to identify the presence of the target materials. In other words, while every wire 12 and molecular recognition reagent 14 combination in the array might react with every target material, the sensor employs computer learning algorithms that will detect different responses of all the wire/reagent combinations and will continually improve as new data regarding the detection of various materials becomes available. As each wire 12 responds differently to each target material, an effective "fingerprint" for each material is generated and the artificial intelligence tool is utilized to interpret the fingerprint and identify the target materials in the target device.

In preferred embodiments, the ferromagnetic wire 12 is an amorphous wire constructed from a ferromagnetic alloy having one or more glass forming components. The amorphous wire is preferably a Cobalt (Co) and/or Iron (Fe) based alloy with representative compositions including $Fe_{77.5}Si_{7.5}B_{15}$, $Co_{80}Si_{10}B_{10}$, $Fe_{73.5}CuNb_3Si_{13.5}B_9$, $Co_{68.15}Fe_{4.35}Si_{12.5}B_{15}$, and $Co_{80.9}Fe_{4.4}Nb_{4.5}Si_{8.7}B_{1.5}$ with a diameter of about 30 to 100 microns. However, the particular combination of components and dimensions of the wire can be tailored for specific applications and an array of sensing elements 10 may include wires of varying alloys and/or diameters including diameters from about 5 to 125 microns. The amorphous characteristic of the wire 12 is produced during the alloy casting operation by rapid cooling from the molten to solid state. As a result, the material has a disordered atomic-scale (noncrystalline) structure. This noncrystalline structure leads to a higher tensile strength than that of material with an orderly structure. Further, the amorphous wire 12 has high magnetic susceptibility with low coercivity and high electrical resistance. Thus, the magnetic domains of the wires 12 can be switched when subjected to very small alternating magnetic fields. In addition, the amorphous wire magnetic domain switching properties are sensitive to stress. These properties of the amorphous ferromagnetic wire 12 enable the sensing applications of the disclosed sensors as further described below.

The amorphous wire 12 is preferably made using a melt extraction process, which forms the wire by passing a sharp spinning blade through a pool of molten alloy metal. Alternatively, the amorphous wire 12 could be made using the so-called Taylor process, which forms the wire by drawing it from a molten glass vial containing the alloy metal. Wires 12 made from the two processes are quite distinctive from each other. The Taylor wire has a glass coating, which melt extraction wire does not have. Glass-coated Taylor wire can also be wound in long lengths whereas melt extracted wire cannot be readily spooled and is generally only available in short lengths up to about 2 meters. In effect, melt extracted wire is less uniform than glass-coated Taylor wire, which can cause calibration differences between different sensing elements. However, despite the non-uniform dimension, one advantage of melt extracted wire over Taylor wire is that it has a greater sensitivity to tension (sensitivity of the melt extracted wire is believed to be over three times greater than the sensitivity of amorphous wire made using the Taylor process), which enables detection of smaller force changes without compromising the size of the sensing element 10. Further, when constructing a sensing element 10 having amorphous wire 12 made using the Taylor process, a preload or pre-stretch (estimated to be up to about 12 grams) is needed to eliminate non-responsiveness of the sensing element 10 (i.e., small increases in tension in insufficiently pre-stretched Taylor wire does not produce a corresponding change in detected peak height). This preload is disadvantageous because pre-stretching of the amorphous wire 12 results in sensor de-calibration for applications where the sensor is deployed for extended periods of time. Use of melt extracted amorphous wire eliminates or significantly reduces this preload requirement. A third benefit of using melt extracted amorphous wire as opposed to Taylor wire is that the melt extracted wire has a higher toleration to stress without de-calibration.

In yet another embodiment, the amorphous wire 12 is constructed using a modified melt spinning process known as "rotating water bath melt spinning" which involves the streaming of a fine jet of molten alloy into a flow of cold water such that the alloy rapidly solidifies and vitrifies. Wire 12 made using this process typically has a diameter of about 80-120 microns and exhibits similar characteristics to melt extracted wire although it is not as sensitive.

The molecular recognition reagents 14 are chosen from reactive materials that are operable to expand upon exposure and/or absorption of vapor and/or liquid from the target materials. The space from which the molecular recognition reagents are chosen is large, and the choice generally depends on the particular target substance (e.g., explosive, chemical or biological warfare agent, pharmaceutical, moisture, etc.) that the sensor is intended to detect and the environment conditions in which the device is to be used. Such molecular recognition reagents include, but are not limited to high molecular-weight polymers, solid-phase microextraction (SPME) materials, metal-organic frameworks (MOFs), immobilized antibodies, classical zeolites, and other porous polymers and metals and combinations thereof. Specific examples of molecular recognition reagents include, without limitation, the following: polyacrylic acid (PAA), polyhydroxyethyl methacrylate, dimethacrylate (EDMA), methacrylic acid (MAA), methyl cellulose, polyethyleneimine (PEI), polyethylene oxide (PEO), polypropylene (PP), polystyrene (PS), polydimethylsiloxane (PDMS), Calix[6]arene (Cal[6]), Heptakis(6-O-tert-butyldimethylsilyl-2,3-di-O-acetyl)-β-cyclodextrin (cyclodextrin or CD), electrospun polymers, Kraton® polymers (a synthetic replacement for rubber), and composites thereof. As mentioned above, the sensing element 10 will preferably employ a diverse set of molecular recognition reagents 14 such that each wire 12 will respond differently to each type of target material absorbed by the molecular recognition reagents 14. Further, the particular configuration of the molecular recognition reagents 14 may vary based on the particular target material to be detected. In this regard, the choice of particular molecular recognition reagents 14 is generally based on considerations such as pore size, pore shape, polarity, etc. as compared to the target materials being detected. For example, in embodiments where the sensor is intended to detect large molecules such as provided in anthrax, the molecular recognition reagent may include an imprintable polymer having a "lock and key" arrangement for targeting the particular shape of anthrax molecules. In other words, in the "lock and key" arrangement, the reagent surface and volume includes specific geometric shapes complementary to the shapes of targeted particles.

It is further noted that molecular recognition reagents 14 may also be fabricated from biological materials such as enzymes, antibodies, and aptamers (small single-stranded DNA or RNA molecules) to have lock-and-key relationships with specific substrates. Also, regarding molecular recognition reagents 14 made from composite materials, some of the materials as identified above are used at least in part to improve the ability to fabricate the molecular recognition reagents 14. This is particularly true of a cyclodextrin/poly (ethylene oxide) (CD/PEO) mixture. In this regard, CD by itself is difficult to be machined into a molecular recognition reagent 14 of a proper shape and size from a pressed disk due to its friability, but addition of a certain amount of PEO makes the material much more workable. Considering that the composite reagents are physical mixtures—that is, they are typically mixed and pressed rather than reacted—countless combinations of molecular recognition reagents 14 are possible, such as the CD/PEO mixture, to detect each different target material.

Figure 2:
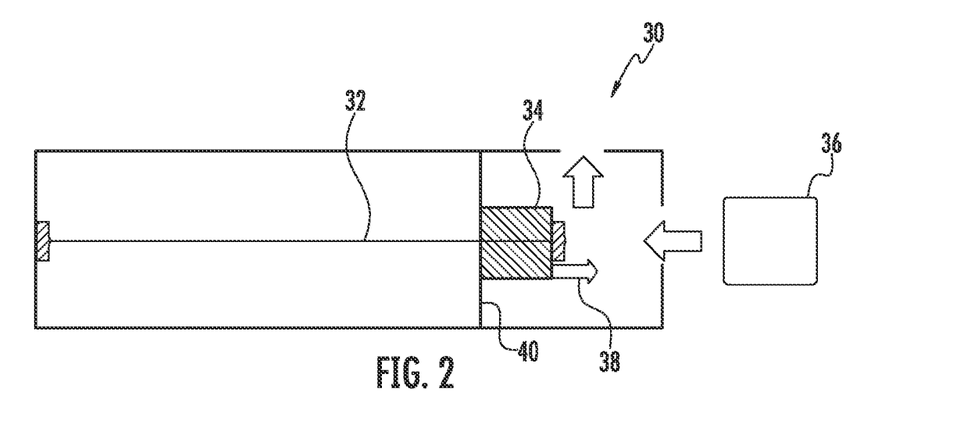

Referring to FIG. 2, an alternate embodiment of a sensing element 30 is shown in which the molecular recognition reagent 34 is secured to both the ferromagnetic wire 32 and a fixed support 40. When detecting a target device, the molecular recognition reagent 34 expands away from the fixed support 40 which imposes stress on the ferromagnetic wire 32 in one direction as indicated by arrow 38. In yet another potential embodiment, the ferromagnetic wire is placed under tension through the use of a tension inducing mechanism such as a spring such that, when the molecular recognition reagent 34 expands upon absorption of a target material 36, the molecular recognition reagent relieves the tension generated by the tension inducing mechanism.

In preferred operation, a sensing element substantially as described above is placed in proximity to a target device such that the molecular recognition reagent of the sensing element expands upon absorption of vapor or liquid from a target material while an inducing mechanism is used to induce alternating magnetic domains in the ferromagnetic wire of the sensor. The expansion of the molecular recognition reagent changes a tensile stress upon the ferromagnetic wire, and a detection mechanism is used to detect changes in the switching properties of the ferromagnetic wire as a function of changes in the tensile stress of the wire.

Figure 3:
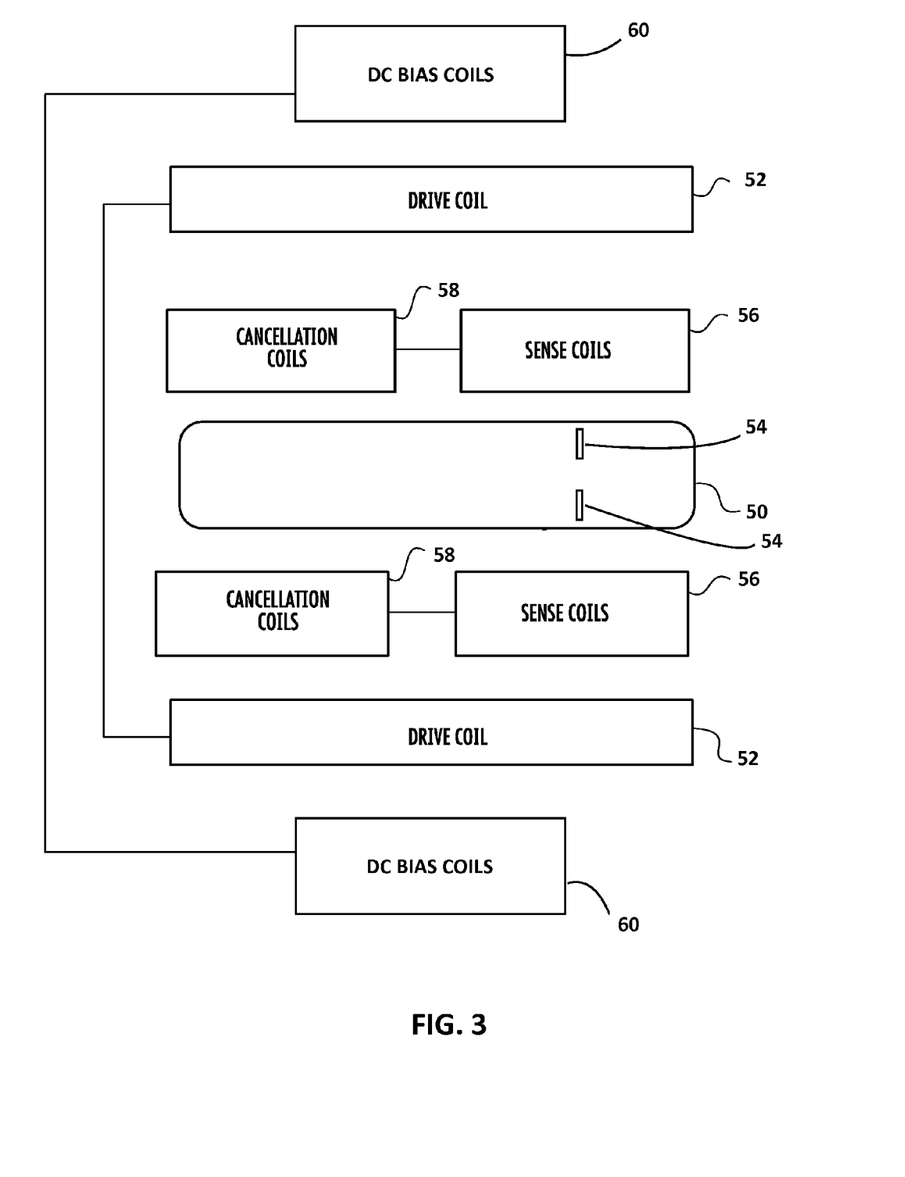
FIG. 3 depicts a schematic illustration of a sensing element detection mechanism according to the present disclosure.

FIG. 3 schematically illustrates a sensor 50 according to the present disclosure where one or more sensing elements 54 are detected by a detection mechanism composed of a system of at least one drive coil 52 and at least one pickup/sensing coil 56. Sensor 50 includes the sensing elements 54 positioned such that changes in the magnetic switching characteristics of the sensing elements 54 caused by changes in the mechanical stress imposed on the wire by the molecular recognition reagent is detected by one or more pickup/sensing coils 56. An alternating current in the drive coil 52 creates the magnetic field, which continually reverses the magnetic domains in the amorphous wire of the sensing elements 54. Reversal of the magnetic domains is detected with the pickup coil 56 as a peak, which changes height based on tensile stress applied to the ferromagnetic wires by the molecular recognition reagents. In other words, target materials are detected by detecting changes in induced peaks along a time waveform resulting from both the induced alternating domains in the ferromagnetic wire 12 and changes in the tensile stress of the wire 12 caused by exposure of the target material to the molecular recognition reagent 14 coupled to wire 12.

In preferred embodiments, the pickup coils 56 are positioned above and around the sensing elements 54. However, orientation of the pickup coils 56 may vary as desired based on the flux line being detected. In certain embodiments, one or more cancellation coils 58 may also be provided that are wired in an opposite direction from pickup coil 56. Cancellation coil 58 detects a similar drive coil magnetic field but does not detect a significant amount of the signal produced by switching of the ferromagnetic wire of sensing elements 54. The purpose of the cancellation coil is to cancel most of the magnetic field produced by the drive coils and eddy currents caused by the drive fields in conducting objects near the pickup coils 56. According to preferred embodiments utilizing a plurality of sensing elements 54, an offsetting direct current bias field generated by DC bias coils 60 may also be employed by the detection mechanism such that the switching of the magnetic domains of each sensing element occurs at slightly different periods along the time domain. This allows the time domain of each sensing element to be isolated for easier measurements of the peak height of each individual sensor by the pickup coils 56. Different configurations of the bias coil set 60 may be used such as a Maxwell coil or a solenoid with varied coil winding density.

Sensing element 54, drive coil 52, pickup coil 56, cancellation coil 58 (if used), and DC bias coil 60 (if used) may be housed within a single unit sensor having a power source and wired or wireless communication means for transmitting data acquired from the sensing element 54, or the drive coil 52, pickup coil 56, cancellation coil 58 (if used), and DC bias coil 60 (if used) may be provided in a separate unit from the sensing element 54.

Benefits of a sensor such as those described above include the fact that the sensing element does not require radioactive sources and, in embodiments where the drive 52 and pickup coils 56 are provided in a separate unit from the sensing element 54, the sensing element does not require any type of physical power source or data transfer connection. Further one pickup coil is capable of detecting multiple sensing elements having various molecular recognition reagents without tedious alignment of the sensing elements. Thus, the sensor is small, inexpensive, and portable while offering the benefits of rapid detection as well as being highly selective and sensitive.

Figure 4A:
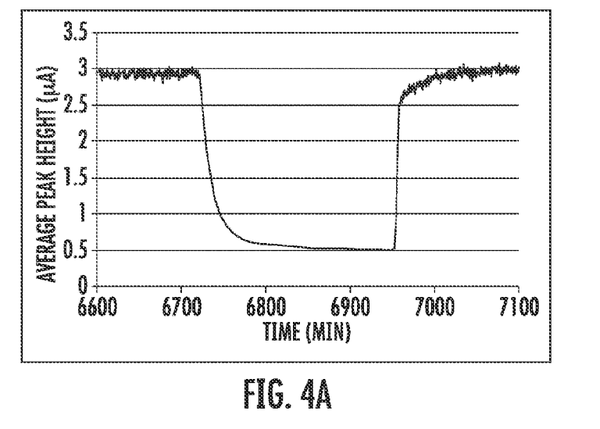
FIGS. 4A-4C depict peak height detection graphs for detecting methanol using a variety of molecular recognition reagents according to the disclosure.
Figure 4B:
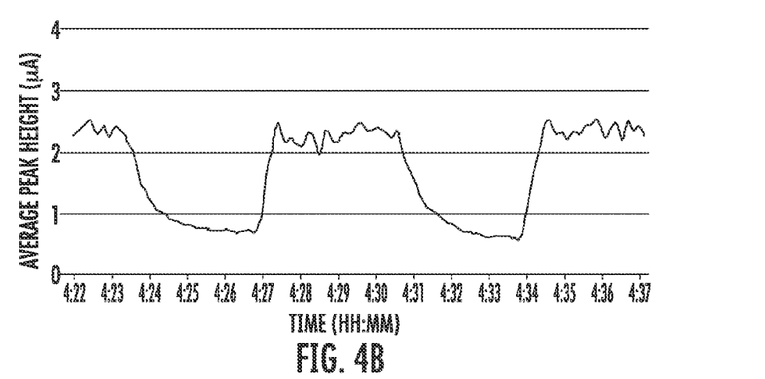
Figure 4C:
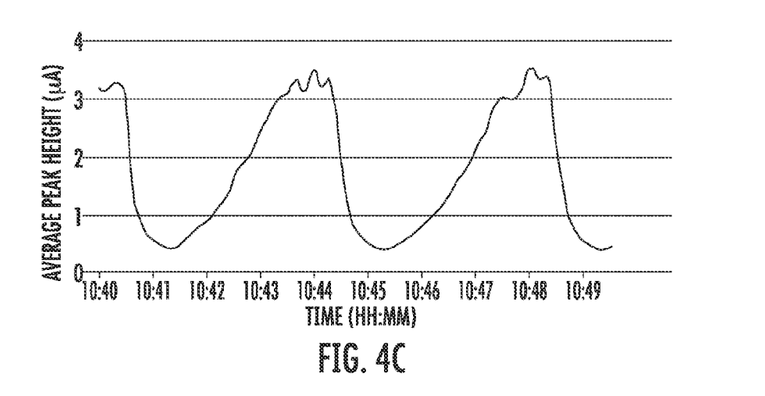

Referring to FIGS. 4A-4C, detection of methanol vapor entrained in a stream of air as an exemplary target material is shown when using a sensing element having various molecular recognition reagents. Referring to FIG. 4A, the molecular recognition reagent is methyl cellulose. Referring to FIG. 4B, the response to methanol of sensing element having a molecular recognition reagent composed of 100% polyethylene oxide (PEO) is provided, whereas FIG. 4C provides the response to methanol where the molecular recognition reagent is composed of 40% α-cyclodextrin and 60% PEO. It is noted that a sensing element having 100% α-cyclodextrin as the molecular recognition reagent is believed not to substantially respond to methanol (i.e., does not create tension in the amorphous wire). The heights of the peaks in the figures are dependent on the speed at which the amorphous wire domains reverse and the strength of the field produced by the wire. As tension is applied to the wire upon absorption of the methanol vapor by the particular molecular recognition reagent, the permeability of the amorphous wire decreases and the domain switching slows.

Additionally, the amplitude of the field produced by the wire may decrease. This causes the peak current in the pickup coil 56 of FIG. 3 to decrease with the increase in tension, which is proportional to the amount and type of target material absorbed by the molecular recognition reagent. Slopes and shapes of the falling and rising signals, delay times, and peak heights detected by the pick-up coil may all be useful in determining the identity and concentration of a target and establishing a "fingerprint" for various target materials.

According to another aspect of the disclosure, and referring again to FIG. 1, sensing element 10 may also be used to detect radiation 16 by coupling the ferromagnetic metal wire 12 to a molecular recognition reagent 14 that changes dimensions as a result of exposure to radiation. In other words, when the "target" is radiation, the ferromagnetic metal wire 12 is coupled to a molecular recognition reagent/radiation sensitive material 14 that is operable to impose a change in stress on the wire 12 upon exposure to radiation. According to this embodiment, housing 20 preferably provides protection to the sensing element 10 from mechanical or chemical damage but is fabricated from a material that is otherwise transparent to the radiation being detected. Thus, while FIG. 1 shows vent holes 29 in the housing 20, these vent holes 29 may be omitted when the "target" is radiation 16. The presence of radiation is then able to be detected using a detection mechanism as described above by detecting changes in induced peaks along a time waveform resulting from induced alternating domains in the ferromagnetic wire 12 and changes in the tensile stress of the wire 12 caused by exposure of radiation to the radiation sensitive material 14 coupled to wire 12.

According to certain embodiments, the radiation sensitive material 14 is operable to expand upon exposure to radiation by using a material in which radiation creates voids/bubbles in the radiation sensitive material, which would impose additional stress upon the wire 12. In other exemplary embodiments, the radiation sensitive material may be selected from materials that lose mechanical strength and/or are damaged upon exposure to radiation, which would cause a pre-stressed wire 12 coupled to the radiation sensitive material to contract/relax. According to some embodiments, the radiation sensitive material is chosen from a material that permanently expands or contracts upon exposure to radiation (e.g., steels) such that exposure to any radiation could be detected. Alternatively, or used in conjunction with a sensing element having a radiation sensitive material that permanently expands/contracts, the wire 12 could be coupled to a radiation sensitive material that gradually expands/contracts upon exposure to radiation (e.g., teflons) to provide a record of cumulative radiation exposure. The effects of radiation on various classes of materials (e.g., metals, ceramics, polymers, biological tissues, etc.) are generally known from the field of radiation materials science. Thus, selection of an appropriate radiation sensitive material may be taken from materials as taught in this field to change the stress of wire 12 as desired.

Figure 5:
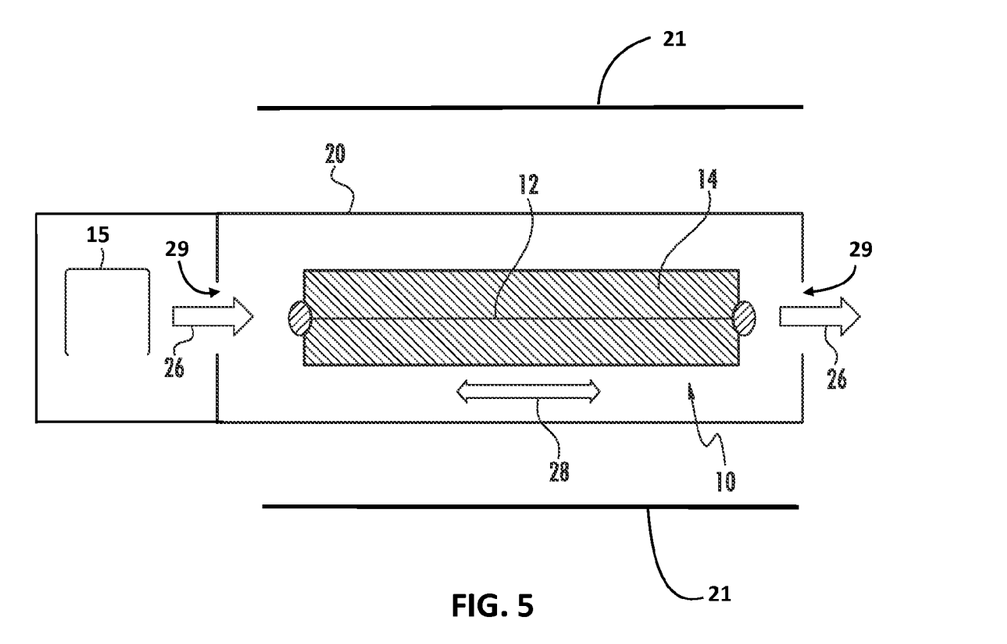
FIG. 5 depicts an alternate embodiment of a radiation sensor according to the disclosure.

Referring to FIG. 5, an alternate embodiment of a radiation sensor is shown in which the wire 12 is directly coupled to a molecular recognition reagent 14 as described above and the radiation sensitive material 15 is disposed adjacent to the sensing element 10. According to this embodiment, the radiation sensitive material is selected from a material that produces a gas upon exposure to radiation (e.g., teflons produce hydrogen fluoride upon exposure to radiation) such that the gas produced by the radiation sensitive material is operable to change a tensile stress of the wire 12 upon exposure of the molecular recognition reagent 14 to the gas emitted from the radiation sensitive material. A radiation shield 21 is preferably provided to protect the chemical sensing element 10 from radiation damage.

In another aspect of the radiation sensor embodiment, the radiation sensing element is operable to distinguish between gamma rays and neutrons by exploiting the fact that gamma rays are increasingly absorbed as the atomic number of an atom increases (lead is an example of a good gamma ray absorber) while neutrons are most efficiently scattered by hydrogen atoms. Thus, a sensing device for efficiently distinguishing neutrons from gamma rays is possible upon selection of appropriate radiation sensitive materials of the sensing elements that react differently to gamma rays and neutrons.

According to yet another embodiment of the radiation sensor, the ferromagnetic metal of the sensing element itself may be configured to incur radiation-induced changes in the ferromagnetic metal alloy, including changes in the alloy's magnetic and physical properties. In particular, the ferromagnetic metal is operable to function as a neutron sensor as a result of the radiation-induced changes in the magnetic properties of an amorphous alloy brought about by the impinging neutrons and by energetic charged particles created from $^{10}B(n, \alpha)^{7}Li$ reactions as described, for example, in "Effects of Neutron Irradiation on Nd—Fe—B Magnetic Properties," *IEEE Transactions on Magnetics,* 24 (1988) 2016 (J. R. Cost et al.), and "Effects of Neutron Irradiation on Magnetic Properties of $Fe_{80}Si_{20}$ Amorphous Alloys," *Phys. Stat. Sol.* (A) 99 (1987) 275 (I. Skorvanek and A. Zentko), both of which are incorporated herein by reference. In connection with the latter reference, it is noted that nearly all displacement damage in an $Fe_{80}Si_{20}$ alloy exposed to a fast 12:10 neutron spectrum with a flux of $2.78 \times 10^{13}$ neutrons $cm^{-2}$ $s^{-1}$ is due to $^{10}B(n, \alpha)^{7}Li$ reactions. Radiation transport simulations performed with the Monte Carlo N-Particle (MCNP) code indicate that approximately 0.19% of thermal neutrons incident upon a 30 micron thick ribbon of $Fe_{40}Ni_{38}Mo_{4}B_{18}$ alloy, a commercially available composition known as METGLAS 2826 MB, would be absorbed. Due to the very short range of the charged reaction products (~2.5 microns for alpha particles and ~0.9 microns for $^{7}Li$), most of the energy from a captured neutron would be deposited within one layer of the ribbon. The MCNP simulations further suggest that a wire ten times thicker should capture about five times more neutrons (i.e., about 1% of incident thermal neutrons would be absorbed in a sensor only 0.3 mm thick). It is further noted that these capture statistics are based upon the natural isotopic ratio of B in the METGLAS 2826 MB composition. If the alloy was enriched in $^{10}B$, the predictions would be even better.

An embodiment in which the amorphous ferromagnetic metal alloy itself functions as the radiation sensitive material would be especially attractive for covert applications as the sensing element could assume any discrete structure (e.g., common objects such as a screw) so it could be dropped off at a suspect location and then later retrieved to test for radiation exposure. Further, this embodiment can be manufactured using any technique that preserves the composition and amorphous nature of the material while not requiring an additional radiation sensitive material or molecular recognition reagent to be coupled to the alloy. Using the detection scheme described above, the sensor would require no on-board power sources or physical connections for power or data transfer. The changes in magnetic properties of the alloy would be persistent and cumulative, making this configuration also attractive as radiation sensitive tags and seals.

The foregoing descriptions of embodiments have been presented for purposes of illustration and exposition. They are not intended to be exhaustive or to limit the embodiments to the precise forms disclosed. Obvious modifications or variations are possible in light of the above teachings. The embodiments are chosen and described in an effort to provide the best illustrations of principles and practical applications, and to thereby enable one of ordinary skill in the art to utilize the various embodiments as described and with various modifications as are suited to the particular use contemplated. All such modifications and variations are within the scope of the appended claims when interpreted in accordance with the breadth to which they are fairly, legally, and equitably entitled.

What is claimed is:

1. A radiation sensor comprising:
 a ferromagnetic metal; and
 a radiation sensitive material indirectly coupled to the ferromagnetic metal via a molecular recognition reagent directly coupled to the ferromagnetic metal, the radiation sensitive material operable to emit a gas upon exposure to radiation such that the molecular recognition reagent changes a tensile stress of the ferromagnetic metal upon exposure to the emitted gas from the radiation sensitive material.

2. The sensor of claim 1 wherein the ferromagnetic metal is an amorphous wire.

3. The sensor of claim 2 wherein the amorphous wire is composed of a cobalt and iron based alloy.

4. The sensor of claim 2 wherein the amorphous wire is composed of an iron based alloy.

5. The sensor of claim 2 wherein the amorphous wire is melt extracted.

6. The sensor of claim 1 further comprising a detection mechanism, the detection mechanism including:
 an inducing mechanism to induce alternating magnetic domains in the ferromagnetic metal; and
 a sensing mechanism to detect changes in magnetic switching characteristics of the ferromagnetic metal caused by the inducing mechanism and changes in the tensile stress of the ferromagnetic metal caused by exposure of the radiation sensitive material to radiation.

7. The sensor of claim 6 wherein the sensing mechanism detects changes in induced peaks along a time waveform resulting from the induced alternating magnetic domains in the ferromagnetic metal and changes in the tensile stress of the ferromagnetic metal.

8. The sensor of claim 6 wherein the detection mechanism is provided in a separate unit from the ferromagnetic metal and the radiation sensitive material.

9. The sensor of claim 6 wherein no electrical components are physically connected to the radiation sensor.

10. A radiation sensor comprising:
 a ferromagnetic metal having a tensile stress that is operable to change upon exposure to radiation;
 a detection mechanism, the detection mechanism including an inducing mechanism to induce alternating magnetic domains in the ferromagnetic metal and a sensing mechanism to detect changes in induced peaks along a time waveform resulting from the induced alternating domains in the ferromagnetic metal and changes in the tensile stress of the ferromagnetic metal caused by exposure of the ferromagnetic metal to radiation.

11. The sensor of claim 10 wherein the ferromagnetic metal is an amorphous material.

12. The sensor of claim 11 wherein the amorphous material is composed of an iron based alloy.

13. The sensor of claim 10 wherein the detection mechanism is provided in a separate unit from the ferromagnetic metal.

14. The sensor of claim 10 wherein no electrical components are physically connected to the ferromagnetic metal.

15. A method of detecting radiation in a target device comprising:
   providing a sensor element including a ferromagnetic metal and a radiation sensitive material indirectly coupled to the ferromagnetic metal via a molecular recognition reagent directly coupled to the ferromagnetic metal;
   placing the sensor element in proximity to or inside the target device such that the radiation sensitive material emits a gas upon exposure to radiation and the molecular recognition reagent changes a tensile stress of the ferromagnetic metal upon exposure to the emitted gas from the radiation sensitive material; and
   detecting a change in magnetic switching characteristics of the ferromagnetic metal resulting from the change in tensile stress imparted by the radiation sensitive material and the molecular recognition reagent.

16. The method of claim 15 wherein the ferromagnetic metal is an amorphous wire.

17. The method of claim 16 wherein the amorphous wire is composed of a cobalt and iron based alloy.

18. The method of claim 15 wherein the detecting step is performed by a detection mechanism configured to wirelessly interrogate the sensor element.

* * * * *